US005654509A

United States Patent [19]
Miele et al.

[11] Patent Number: 5,654,509
[45] Date of Patent: Aug. 5, 1997

[54] CONTROL SYSTEM THAT DISTINGUISHES BETWEEN IMAGING AND NONIMAGING ENVIRONMENTS IN AN ULTRASOUND SYSTEM

[75] Inventors: Frank R. Miele, Methuen; Ronald Mucci, Westwood, both of Mass.

[73] Assignee: Hewlett-Packard Company, Palo Alto, Calif.

[21] Appl. No.: 647,082

[22] Filed: May 8, 1996

[51] Int. Cl.$^6$ .......................... G01N 29/06; G01N 29/22
[52] U.S. Cl. .................. 73/602; 73/626; 73/628; 73/1.82; 128/660.07; 128/661.01; 364/DIG. 1
[58] Field of Search .................. 73/625, 626, 633, 73/602, 628, 629, 631, 641, 1 DV; 128/660.01, 660.07, 660.08, 661.01, 662.03, 662.02; 601/2; 367/96; 395/750; 364/267, 267.9, 273.1, 273.2, 273.3, 550, 707, DIG. 1

[56] References Cited

U.S. PATENT DOCUMENTS

| | | | |
|---|---|---|---|
| 3,552,520 | 1/1971 | Naubereit | 367/197 |
| 3,578,990 | 5/1971 | Naubereit | 327/227 |
| 3,619,657 | 11/1971 | Naubereit | 327/392 |
| 4,945,767 | 8/1990 | Shirasaka | 73/610 |
| 5,416,726 | 5/1995 | Garcia-Duarte et al. | 364/550 |
| 5,482,046 | 1/1996 | Deitrich | 128/662.02 |
| 5,504,910 | 4/1996 | Wisor et al. | 395/750 |

*Primary Examiner*—Hezron E. Williams
*Assistant Examiner*—Rose M. Miller
*Attorney, Agent, or Firm*—John L. Imperato

[57] ABSTRACT

In the present invention, a control system uses acoustic data produced by an ultrasound system to assess whether the acoustic environment presented to the ultrasound system's transducer is an imaging environment, such as patient's body, or a nonimaging environment, such as air. Various operating parameters of the ultrasound system may be controlled based on the assessment. In the nonimaging environment, the control system reduces the amplitude of a drive signal applied to the transducer, substantially reducing power dissipation in the transducer. The control system detects a transition to the imaging environment and returns the drive signal to the amplitude used in the previous imaging environment. If the nonimaging environment persists for greater than a predetermined time period, the control system initiates a standby mode which substantially reduces power consumption by the ultrasound system. The control system is readily integrated into the imaging stream of an ultrasound system.

21 Claims, 3 Drawing Sheets

CONTROL SYSTEM THAT DISTINGUISHES BETWEEN IMAGING AND NONIMAGING ENVIRONMENTS IN AN ULTRASOUND SYSTEM

FIELD OF THE INVENTION

The present invention relates to medical ultrasound systems and, more particularly, to a control system incorporated into an ultrasound system that uses acoustic data to distinguish between imaging and nonimaging environments. Various operating parameters in the ultrasound system may be controlled according to the acoustic environment assessed by the control system.

BACKGROUND OF THE INVENTION

Medical ultrasound systems are used by physicians and technicians in a variety of clinical situations to ultrasonically view organs and tissues within a patient's body. Although the ultrasound systems may be used sporadically in a hospital or other clinical setting, the systems are often left with the power on, ready for use by a physician or technician.

When the ultrasound system is left on with a high amplitude drive signal applied to the system's transducer, the power dissipation in the transducer is high. If the high power dissipation persists for prolonged time periods, the performance of the transducer degrades and the reliability of the transducer is diminished. In addition, ultrasound systems have high power consumption, making the systems expensive to operate. If a system is turned off in an effort to reduce power consumption, when the system is turned back on, a time delay may result before the system is again ready for use. The time delay may be caused by booting-up the system's software, by running self-diagnostic tests, or by waiting for components in the system to respond once power is applied.

In presently available ultrasound systems, power dissipation in the transducers may be reduced by decreasing the amplitude of the drive signal applied to the transducer. However, the reduced drive signal amplitude provides lower acoustic returns at the transducer which degrade the quality of the ultrasonic images produced by the ultrasound system.

SUMMARY OF THE INVENTION

In the present invention, a control system improves the reliability of transducers, reduces power consumption in ultrasound systems and enables an ultrasound system to produce high quality images. The control system uses acoustic data produced by an ultrasound system to assess whether the acoustic environment presented to the transducer is an imaging environment, such as patient's body, or a nonimaging environment, such as air.

Once the acoustic environment is assessed, various operating parameters of the ultrasound system may be controlled according to the assessed acoustic environment. For example, in the nonimaging environment, the control system substantially reduces the amplitude of the drive signal applied to the ultrasound system's transducer. This reduces power dissipation and heating of the transducer. When use of the ultrasound system commences, the control system detects the imaging environment and returns the drive signal to the amplitude used in the previous imaging environment. If the nonimaging environment persists for greater than a predetermined time period, the control system initiates a standby mode which substantially reduces power consumption by the ultrasound system.

Power dissipation in the transducer is substantially reduced in the nonimaging environment, improving the transducer's reliability and performance. In the imaging environment, the drive signal amplitude may be maximized, enabling the ultrasound system to produce high quality images. The control system is readily integrated into the imaging stream of an ultrasound system, without increasing the manufacturing cost of the ultrasound system or the transducer.

DETAILED DESCRIPTION OF THE PREFERRED EMBODIMENT

Figure 1:
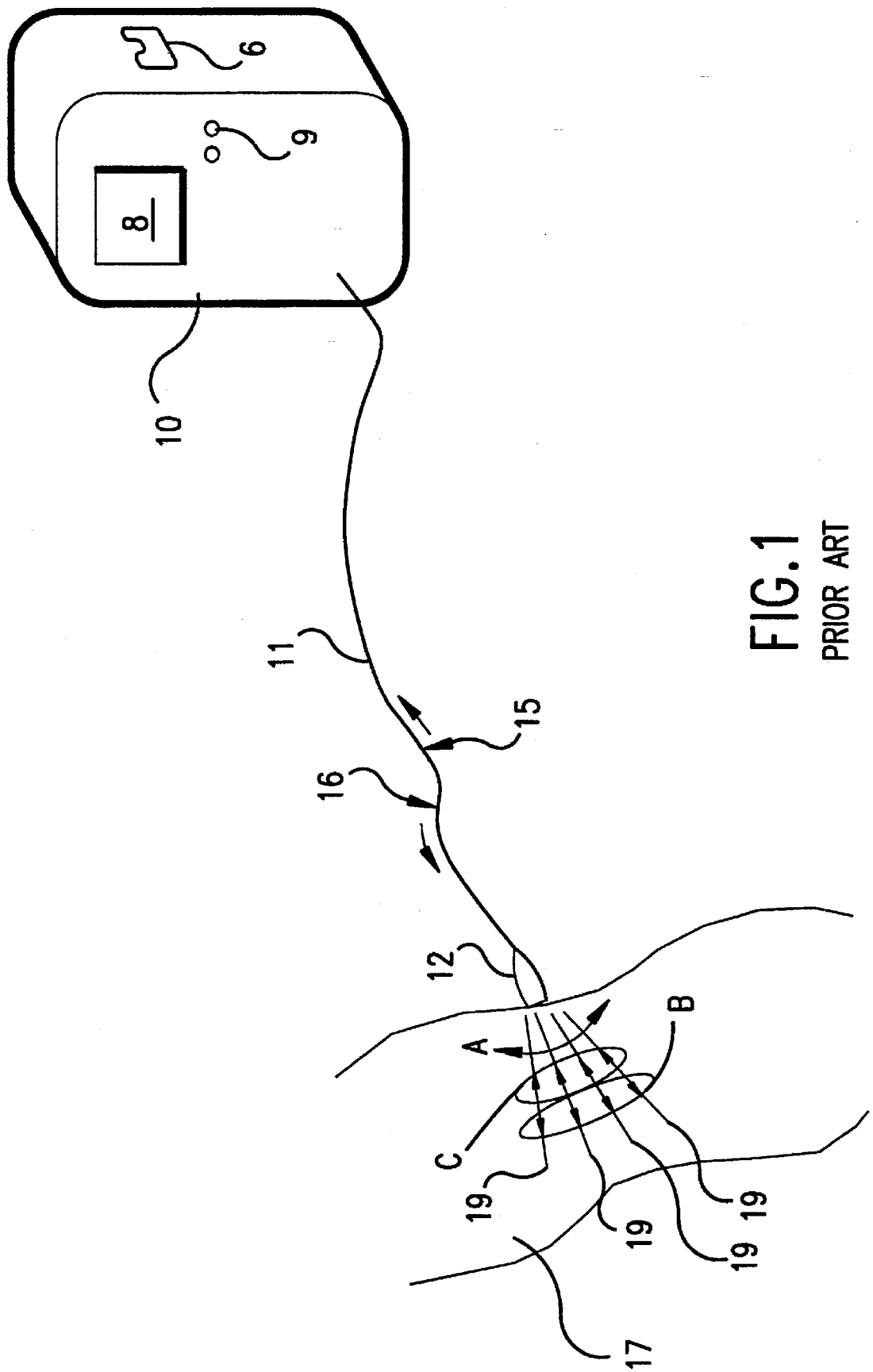
FIG. 1 shows a prior art medical ultrasound system and transducer.

FIG. 1 shows a prior art medical ultrasound system 10. A cable 11 couples an ultrasound transducer 12 to the ultrasound system 10. The transducer 12 produces an acoustic beam B in response to an electrical drive signal 16 provided by the ultrasound system 10.

The acoustic beam B is repetitively swept in the directions of arrow A, across an acoustic medium, such as a sector of a patient's body 17. The transducer 12 is placed in contact with a patient's body 17 and the swept acoustic beam B enters the patient's body 17 along a series of trajectories, or acoustic lines 19. The acoustic beam B is partially reflected by various structures within the patient's body 17, forming an acoustic return C which propagates back toward the transducer 12. The transducer 12 intercepts the acoustic return C and produces a received electrical signal 15 in response to the acoustic return C. The received electrical signal 15 is applied to a receiver (not shown) in the ultrasound system 10 where it is processed as acoustic data. This acoustic data is then stored in a memory (not shown). The acoustic data corresponds to the acoustic return C along each of the acoustic lines 19 and the acoustic data is updated according to the acoustic return received from the acoustic medium. The acoustic data is further processed and scan converted within the ultrasound system 10 to form ultrasonic images on a display 8. The imaging stream of the ultrasound system includes the receiver, memory, a scan converter and the display 8.

Inevitably, at the end of an imaging sequence or due to an interruption in the imaging sequence, the transducer 12 is removed from contact with the patient's body 17 and stored in a holder 6 or other nonimaging environment in which the acoustic medium, such as air, produces significantly less time-varying acoustic data than the acoustic data acquired from a patient's body 17. The amplitude of the drive signal 16, which may be adjusted using a gain control knob 9, is often left at the high amplitude setting used in the previous imaging environment. Since the acoustic impedance of the transducer 12 is impedance matched to biological tissue, which differs greatly from that of air, most of the acoustic power in the acoustic beam B is reflected back into the transducer 12 at the transducer-air interface. The acoustic power is dissipated in the transducer 12, resulting in unnecessary heating of the transducer.

Figure 2:
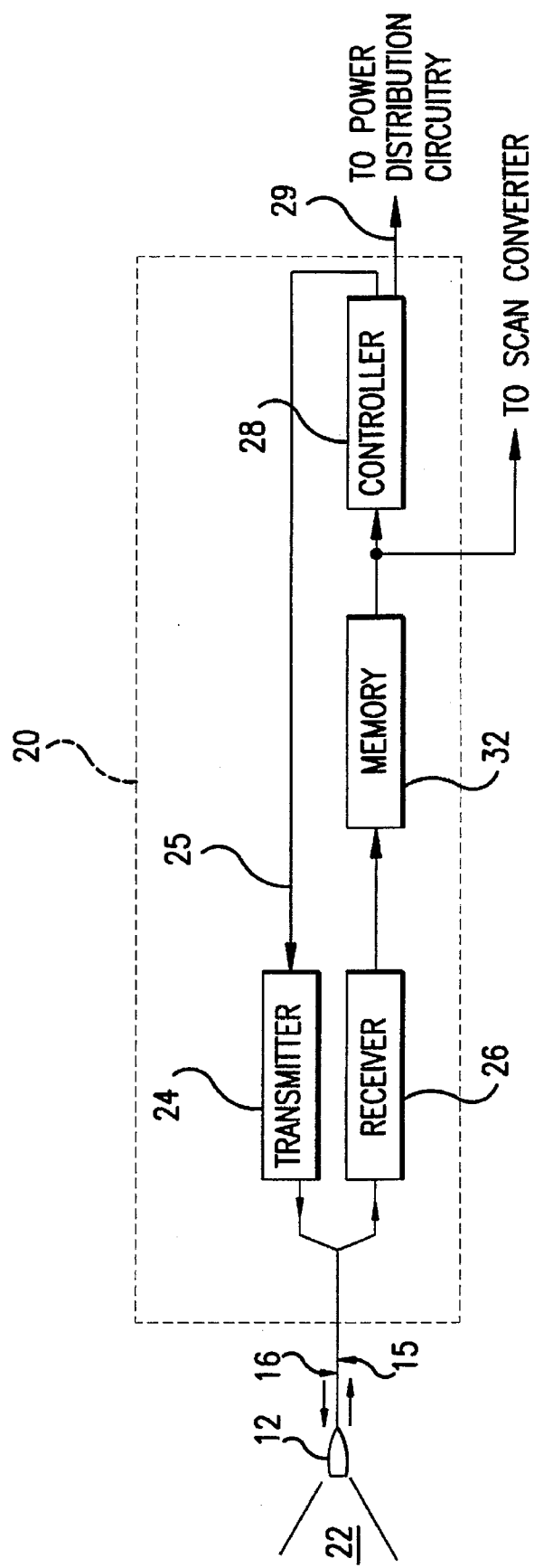
FIG. 2 shows a control system constructed in accordance with the preferred embodiment of the present invention.

FIG. 2 shows a control system 20 that is constructed in accordance with a preferred embodiment of the present invention. The control system 20 may be implemented using hardware or software, and is readily incorporated into the imaging stream of presently available ultrasound systems 10. A controller 28 within the control system 20 uses acoustic data produced by the ultrasound system, which corresponds to the acoustic return C received by the transducer 12, to assess whether the acoustic medium 22 is a patient's body 17 (imaging environment) or air (nonimaging environment).

When the nonimaging environment is detected, the controller 28 provides a disable signal on control line 25 to a transmitter 24 within the ultrasound system 10. In response to the disable signal, the transmitter 24 substantially reduces the amplitude of the drive signal 16 applied to the transducer 12. The amplitude of drive signal 16 is reduced enough for the power dissipation in the transducer 12 to be negligible, avoiding heating of the transducer 12. Although substantially reduced in amplitude, the drive signal 16 produces enough acoustic power to provide an acoustic return C, sufficient for the controller 28 to detect transitions from the nonimaging environment to the imaging environment.

When the transducer 12 is placed in contact with a patient's body 17, the controller 28 detects the imaging environment and provides, to the transmitter 24, an enable signal on control line 25. In response to the enable signal, the transmitter 24 returns the drive signal 16 to the amplitude setting used in the previous imaging environment.

When the nonimaging environment persists for greater than a predetermined time period, the controller 28 provides a standby signal 29, causing the ultrasound system 10 to go into a standby mode. In the standby mode, the standby signal 29 is used by power distribution circuitry within the ultrasound system to interrupt power to most of the components in the ultrasound system 10. However, enough of the components in the ultrasound system 10 are left powered-up to assure that the ultrasound system 10 can return to the operating settings used in the previous imaging environment in substantially less time than it takes for the entire ultrasound system 10 to power-up. Thus, the ultrasound system's 10 software is kept operational in the standby mode to avoid having to boot-up the software when the standby mode is exited. The standby mode reduces power consumption in the ultrasound system 10 and the reduced power consumption increases the ultrasound system's reliability. Adjustments to the gain control knob 9 or to other settings on the ultrasound system 10 "wake up" the ultrasound system 10 from the standby mode and return the operating settings of the ultrasound system 10 to those used in the previous imaging environment.

In order to assess the acoustic medium 22, or acoustic environment, presented to the transducer 12, the control system 20 uses the acoustic data corresponding to the acoustic returns C intercepted by the transducer 12. A first data set is formed using a subset of the acoustic data. The first data set contains acoustic data from the acoustic return C corresponding to one or more of the acoustic lines 19 within a sweep of the acoustic beam B.

A second data set is formed, also using a subset of the acoustic data, but the acoustic data of the second data set is from an acoustic return C resulting from a subsequent sweep of the acoustic beam B. The second data set is selected to contain acoustic data corresponding to the one or more acoustic lines 19 represented in the first data set, but at a later time. For the acoustic lines 19 from the first and second data sets to coincide at equivalent positions, but within different sweeps of the acoustic beam B, the first and second acoustic data sets are derived from the acoustic returns C at time intervals temporally spaced by multiples of the sweep period T of the acoustic beam B. For example, when the first data set is obtained from the acoustic return C in the time interval between time $t_1$ and time $t_2$, the second acoustic data set is obtained from the acoustic return C in the time interval between times $t_1+XT$ and time $t_2+XT$, where X is a positive integer. The first and second data sets are updated continuously, as new acoustic data is continuously stored in a memory 32. For ease of integrating the control system 20 into the imaging stream of presently available ultrasound systems 10, the first and second data sets comprise a subset of the acoustic data which is applied to a scan converter (not shown) within the ultrasound system 10 of an ultrasound system and used to produce ultrasonic images on the display 8.

Differences between the first and second data sets may be attributable to time variability of the acoustic medium 22 or to motion of the transducer 12 that occurs between different sweeps of the acoustic beam B. This time variability of the acoustic medium 22, as represented by the differences between the first and second data sets, provides the basis for detecting whether the transducer 12 is operating in an imaging environment, in which the acoustic medium 22 is a patient's body 17, or in a nonimaging environment, in which the acoustic medium may be air.

In the imaging environment, differences between the first and second data sets are attributable to relative motion within the portion of the patient's body 17 that is being ultrasonically viewed. The acoustic medium 22 may be highly time varying, causing large differences between data sets, as results when the beating heart of a patient is being ultrasonically viewed. When ultrasonically viewing slowly moving organs as found in a patient's abdomen, such as the liver or gall bladder, moderate differences between the data sets result.

In contrast to the imaging environment, the nonimaging environment produces small differences between the first and second data sets. When the transducer 12 is set down or stored in a holder 6, the acoustic medium 22 is typically air. In air, most of the acoustic beam B is reflected at the transducer-air interface, producing small variations between the data sets. Other acoustic environments that are static or significantly less time varying than a patient's body 17 also produce small differences between the data sets.

The controller 28 subtracts the first and second data sets on a point by point basis and takes the magnitude of the differences, or absolute difference, to form a difference set. The difference set is then compared to a decision criteria by the controller 28 to make a preliminary assessment of the acoustic environment. An empirically established decision criteria may be used, based on categorizing difference sets obtained from a variety of trial imaging environments and trial nonimaging environments. The trial imaging environments may include placing the transducer 12 in contact with a patient's body 17 to ultrasonically view the abdomen, kidney, liver, heart and blood vessels at various transmitter 24 and receiver 26 gain settings. The trial nonimaging environments may include the transducer 12 while being hand-held, draped over the ultrasound system 10 and in a holder 6 at a variety of transmitter 24 and receiver 26 gain settings, with and without an impedance matching gel applied to the transducer. The difference sets from the various trial imaging and trial nonimaging environments are used to establish decision criteria which are then used to detect whether an imaging environment or a nonimaging environment is presented to the transducer 12.

The decision criteria used in the preferred embodiment of the present invention includes a lower threshold, an upper threshold and a mean weighted threshold. The controller 28 compares each difference set to the decision criteria to make an assessment of the acoustic environment. Difference sets which have values below the lower threshold are assessed as nonimaging environments, while difference sets which have values above the upper threshold are assessed as imaging environments. A mean weighting of the values in the difference set is employed for intermediate difference sets, whose values lie above the lower threshold but below the upper threshold. For these intermediate difference sets, each value in the difference set is divided by the mean of the values in the data sets, to form a mean weighted difference set. The mean weighted difference set is then compared to a mean weighted threshold to make an assessment of the acoustic environment. The mean weighted threshold is established empirically by categorizing difference sets that have been mean weighted from the trial imaging environments and trial nonimaging environments. Mean weighting reduces the effects of transmitter 24 and receiver 26 gain settings on the intermediate difference sets.

Image-formatted acoustic data produced at the output of the ultrasound system's 10 scan converter (not shown) or acoustic data at other locations within the imaging stream of the ultrasound system 10 may also be used to form the first and second data sets. Observation of image-formatted acoustic data from the various trial imaging and trial nonimaging environments would be used to establish the decision criteria. The image-formatted acoustic data would then be compared to the decision criteria to assess the acoustic environment.

The reliability of the decision criteria used to make the preliminary assessment of the acoustic environment is determined by measuring the error rate, or percentage of incorrect assessments by the controller 28 as the transducer 12 is used in a variety of acoustic environments and imaging applications. In order to reduce the error rate in the assessment of the acoustic environment, a hierarchial decision structure is used to make a final assessment of the acoustic environment.

Figure 3:
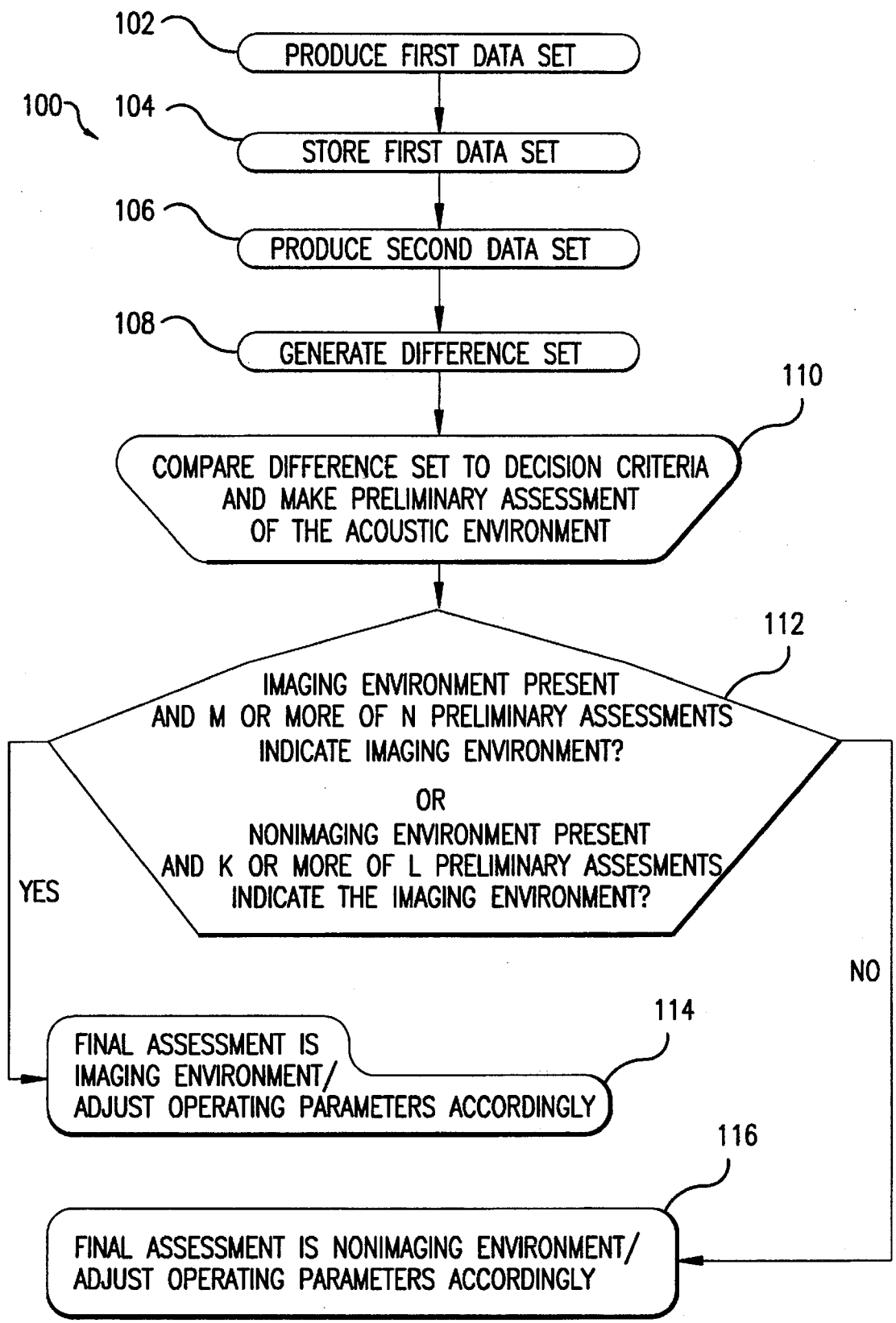
FIG. 3 shows a flow diagram of a decision structure used by the control system of FIG. 2.

FIG. 3 shows a flow diagram 100 of the hierarchial decision structure used by the control system 20. Errors in the final assessment of the acoustic environment are minimized by basing the final assessment on a series of preliminary assessments. In step 102 of flow diagram 100, the first data set is produced from acoustic data derived from the received electrical signal 15 corresponding to the acoustic return C. The first data set is stored in memory 32, in step 104. In step 106, the second data set is produced from acoustic data derived from the received electrical signal 15 corresponding to the acoustic return C from a subsequent sweep of the acoustic beam B. In step 108, the first and second data sets are subtracted on a point by point basis and the magnitude of the difference, or absolute difference, is taken to generate a difference set. In step 110 the difference set is compared to a decision criteria and a preliminary assessment of the acoustic environment is made, based on the comparison. The assessment as to whether the acoustic environment is the imaging environment or the nonimaging environment is also recorded in step 110. The first data set, the second data set and the resulting difference sets produced in steps 102–108 are updated periodically as new acoustic data is generated in the imaging stream of the ultrasound system 10, as the acoustic beam B sweeps.

In step 112, a final assessment of the acoustic environment is made using the results from a series of preliminary assessments made and recorded in step 110. The number of prior preliminary assessments used to make a final assessment of the acoustic environment depends on the present acoustic environment. In the imaging environment, N (N is a positive integer) of the prior preliminary assessments are used. When M (M is a positive integer less than or equal to N), or more, of the N preliminary assessments recorded in step 110 indicate the imaging environment, the final assessment is made in step 114 that the acoustic environment is the imaging environment. When fewer than M of the N preliminary assessments indicate the imaging environment, the final assessment is made in step 116 that the acoustic environment is the nonimaging environment.

In step 112, if the nonimaging environment is present, L (L is a positive integer) of the prior preliminary assessments are used. When K, or more, (K is a positive integer less than or equal to L) of the L prior preliminary assessments recorded in step 110 indicate the imaging environment, the final assessment is made in step 114 that the acoustic environment is the imaging environment. When fewer than K of the L prior preliminary assessments indicate the imaging environment, the final assessment is made in step 116 that the acoustic environment is the nonimaging environment. Once the final assessment of the acoustic environment is made in steps 114 or 116, a variety of the ultrasound system's 10 operating parameters may be controlled, according to the assessment. For example, if the nonimaging environment is assessed in step 116, the amplitude of the drive signal 16 applied to the transducer 12 may be substantially decreased to reduce power dissipation and heating in the transducer 12, which improves the transducer's reliability. If the imaging environment is assessed in step 114, the amplitude of the drive signal 16 applied to the transducer 12 may be increased to optimize image quality in the ultrasound system 10. If the final assessment of the nonimaging environment is made in step 116, and the nonimaging environment persists for longer than a predetermined time period, power consumption by the ultrasound system 10 may be greatly reduced by entering the standby mode. The standby mode improves the reliability of the ultrasound system 10 and the reduced power consumption also makes the ultrasound system 10 less expensive to operate.

The final assessment of the acoustic environment made in step 114 or step 116 may also be used for compliance to imposed standards or guidelines established to limit the time duration during which acoustic power may be applied to a patient, to limit the temperature rise that the patient's tissue can endure, or to comply with other restrictions related to use of ultrasound systems 10. The final assessment of the acoustic environment may be used in conjunction with thermal models developed for the transducer 12, and the patient's tissue surrounding the transducer 12, to provide an "operating history" of the acoustic power applied to the patient's body.

Typically, L, the number of preliminary assessments used in the nonimaging environment, is chosen to be less than N, the number of preliminary assessments used in the imaging environment. This enables the controller 28 to detect transitions from the nonimaging environment to the imaging environment in a shorter time period than it detects transitions from the imaging environment to the nonimaging environment. When in the imaging state, it may be desirable to have the controller 28 take many seconds or even minutes to detect the nonimaging environment and adjust the ultrasound system's 10 parameters according to the final assessment. However, when in the nonimaging state, it may be unacceptable for the controller 28 to take greater than one second to detect the imaging environment and adjust the ultrasound system's 10 operating parameters according to the final assessment when a physician or technician attempts to use the ultrasound system 10. Thus, N, the number of preliminary assessments used in the imaging environment, is greater than L, the number of preliminary assessments used in the nonimaging environment. The error rate in the final assessment of the acoustic environment generally decreases as N and L increase. The final assessment of the acoustic environment may be made more or less immune to occasional variations in the preliminary assessments recorded in step 110 as K is adjusted relative to L, and as M is adjusted relative to N.

When the ultrasound system 10 is used for spectral Doppler ultrasound, the acoustic beam B, shown in FIG. 1, is not swept in the direction of arrow A, but is repeatedly transmitted along a single acoustic line 19. The acoustic data is formed from the acoustic return C along the acoustic line 19 and is updated according to each transmission of the acoustic beam B. Instead of forming a first and second data set from the acoustic data, a statistical analysis of the spectrum of the acoustic data corresponding to the acoustic return C along the acoustic line 19 is performed to assess the acoustic environment. First, the mean and variance of the noise spectrum of the acoustic data is estimated using known techniques. Then, the signal spectrum of the acoustic data is measured. Comparison of the signal spectrum to the mean and variance of the noise spectrum is used to make a preliminary assessment of the acoustic environment. Steps 112 thru 116 of the hierarchial decision structure shown in FIG. 3 are then used to make a final assessment of the acoustic environment.

In summary, the control system 20 is readily incorporated into the imaging stream of an ultrasound system 10. Data sets are readily obtained from the acoustic data or from data elsewhere in the imaging stream, which receives, stores, scan converts and processes the data to form ultrasonic images on the display 8. The controller 28 may comprise the ultrasound system's microprocessor, programmed to form the first and second data sets, compute the difference sets from the data sets, and execute the flow diagram 100 of the hierarchial decision structure to make a final assessment of the acoustic environment. Alternatively, in spectral Doppler ultrasound, the controller 28 may be programmed to estimate the mean and variance of the noise spectrum of the acoustic data and to execute the flow diagram 100 of the hierarchial decision structure to make a final assessment of the acoustic environment.

The control system 20 reduces power dissipation in transducers 12, and reduces power consumption in ultrasound systems 10. Image quality in ultrasound systems 10 is optimized by providing a high amplitude drive signal 16 in the imaging environment, without increasing the manufacturing cost of the ultrasound system 10 or the transducer 12.

What is claimed is:

1. A control system for assessing an acoustic environment of a transducer based on acoustic returns from the acoustic environment, comprising:

an ultrasound system coupled to the transducer transmitting acoustic signals into the acoustic environment and receiving the acoustic returns, the ultrasound system having a set of operating parameters associated therewith, the ultrasound system being operative to generate a series of acoustic data wherein each of the series corresponds to an acoustic return; and a controller coupled to the ultrasound system, comparing one of the series of the acoustic data to another of the series of the acoustic data and generating a control signal based on the comparison, whereby at least one operating parameter of the ultrasound system is adjusted according to the control signal.

2. The control system of claim 1 wherein the controller generates a standby signal to reduce power consumption by the ultrasound system.

3. The control system of claim 1 wherein the controller compares one of the series to another of the series by forming a first data set from one of the series, by forming a second data set from the another of the series and by taking the absolute difference of values in the first data set and values in the second data set, wherein the control signal has a disable state when the absolute difference is less than a lower threshold and wherein when the standby signal is generated when the disable state persists for greater than a predetermined period.

4. The control system of claim 3 wherein the control signal has the disable state when the absolute difference of the values in the data sets, divided by the mean of the values in the data sets, is less than a mean weighted threshold.

5. The control system of claim 4 wherein the control signal has an enable state when the absolute difference of the values in the data sets is greater than an upper threshold, when the absolute difference of the values in the data sets, divided by the mean of the values in the data sets is greater than the mean weighted threshold and when the absolute difference of the values in the data sets, divided by the mean of the values in the data sets, is equal to the mean weighted threshold.

6. A control system for assessing an acoustic environment presented to a transducer comprising:

a receiver coupled to the transducer, receiving a received signal from the transducer in response to an acoustic return from the acoustic environment, and producing acoustic data from the received signal;

a memory, coupled to the receiver, storing the acoustic data, wherein the acoustic data is periodically updated according to the acoustic return;

a controller coupled to the memory, forming one data set from one update of the acoustic data and forming a second data set from another update of the acoustic data, the controller comparing values in the data sets to produce a control signal based on the comparison; and a transmitter coupled to the transducer and to the controller, receiving the control signal and applying a drive signal to the transducer according to the control signal.

7. The control system of claim 6 wherein the control signal adjusts the amplitude of the drive signal.

8. The control system of claim 6 wherein the controller generates a standby signal used to reduce power consumption by the transducer, the receiver and the transmitter.

9. The control system of claim 7 wherein the controller compares values in the data sets by taking the absolute difference of values in the first data set and values in the second data set to form a difference set, wherein the control signal has a disable state when values in the difference set are less than a lower threshold, and wherein the amplitude of the drive signal is substantially reduced when the control signal has the disable state.

10. The control system of claim 9 wherein the standby signal is generated when the disable state persists for greater than a predetermined period.

11. The control system of claim 9 wherein the absolute difference of the values in the data sets divided by the mean of the values in the data sets forms a mean weighted difference set and wherein the control signal has the disable state when the values in the mean weighted difference set are less than a mean weighted threshold.

12. The control system of claim 11 wherein the control system has an enable state when values in the difference set are greater than an upper threshold and when the mean weighted difference set is greater than the mean weighted threshold and when the mean weighted difference set is equal to the mean weighted threshold.

13. The control system of claim 7 wherein the controller compares values in the N, first and second data sets, by taking the absolute difference of a series of N, first and second data sets, to form a series of N difference sets, wherein the control signal has a disable state when fewer then M of the N difference sets have values greater than an upper threshold, and M is an integer not greater than N, and wherein the amplitude of the drive signal is substantially reduced when the control signal has the disable state.

14. The control system of claim 13 wherein the controller compares values in the data sets by taking the absolute difference of a series of L, first and second data sets, to form a series of L difference sets, wherein the control signal has the disable state when fewer than K of the L difference sets have values less than the upper threshold, and K is an integer not greater than L, and L is an integer less than N.

15. The control system of claim 14 wherein the controller generates a standby signal used to reduce power consumption by the transducer, the receiver and the transmitter when the disable state is present for greater than a predetermined period.

16. A control system for assessing an acoustic environment presented to a transducer, comprising:

a receiver coupled to the transducer, receiving a received signal from the transducer in response to an acoustic return from the acoustic environment, and producing acoustic data from the received signal;

a memory, coupled to the receiver, storing the acoustic data, wherein the acoustic data is periodically updated according to the acoustic return;

a controller coupled to the memory, forming a data set from an update of the acoustic data, the controller analyzing the values in the data set and producing a control signal based on the analysis;

a transmitter coupled to the transducer and to the controller, receiving the control signal and applying a drive signal to the transducer according to the control signal;

wherein the control signal adjusts the amplitude of the drive signal; and wherein the controller estimates a mean and a variance of a noise spectrum of the data set and measures a signal spectrum of the data set, and wherein the control signal substantially reduces the amplitude of the drive signal when the amplitude of the signal spectrum is within a predetermined percentage of the variance about the mean of the noise spectrum.

17. The control system of claim 16 wherein the controller generates a standby signal used to reduce power consumption by the transducer and the transmitter when the amplitude is substantially reduced for greater than a predetermined period.

18. A method for assessing an acoustic environment of a transducer coupled to an ultrasound system based on acoustic returns from the acoustic environment, the ultrasound system having operating parameters associated therewith, the method comprising the steps of:

receiving acoustic returns from the acoustic environment;

generating a series of acoustic data, wherein each of the series corresponds to an acoustic return;

comparing one of the series of the acoustic data to another of the series of the acoustic data;

generating a control signal based on the comparison; and adjusting at least one operating parameter of the ultrasound system according to the control signal.

19. The method of claim 18 further comprising the step of generating a standby signal to reduce power consumption by the ultrasound system.

20. The method of claim 19 wherein the step of comparing one of the series of the acoustic data to another of the series of the acoustic data, further includes the steps of forming a first data set from the one of the series, forming a second data set from the another of the series and taking the absolute difference of values in the first data set and values in the second data set, whereby the control signal has the disable state when the absolute difference is less than a lower threshold and the standby signal is generated when the disable state persists for greater than a predetermined period.

21. The method of claim 20 whereby the control signal has the disable state when the absolute difference of the values in the data sets, divided by the mean of the values in the data sets, is less than a mean weighted threshold.

* * * * *